(12) United States Patent
Giblin et al.

(10) Patent No.: US 7,173,047 B2
(45) Date of Patent: Feb. 6, 2007

(54) BENZO (F) INSOINDOL DERIVATIVES AND THEIR USE AS EP4 RECEPTOR LIGANDS

(75) Inventors: Gerard Martin Paul Giblin, The Frythe (GB); Stephen Vernon Frye, North Carolina, NC (US); Susan Roomans, Stevenage (GB)

(73) Assignee: Glaxo Group Limited, Greenford (GB)

( * ) Notice: Subject to any disclaimer, the term of this patent is extended or adjusted under 35 U.S.C. 154(b) by 514 days.

(21) Appl. No.: 10/450,639

(22) PCT Filed: Dec. 20, 2001

(86) PCT No.: PCT/GB01/05706

§ 371 (c)(1),
(2), (4) Date: Dec. 10, 2003

(87) PCT Pub. No.: WO02/50033

PCT Pub. Date: Jun. 27, 2002

(65) Prior Publication Data

US 2004/0087624 A1    May 6, 2004

(30) Foreign Application Priority Data

Dec. 21, 2000   (GB) ................... 0031295.9

(51) Int. Cl.
*A61K 31/403*   (2006.01)
*C07D 209/60*   (2006.01)

(52) U.S. Cl. ............ 514/339; 548/215; 548/243; 548/416; 548/427; 548/450; 546/276.7; 514/374; 514/378; 514/411

(58) Field of Classification Search ........ 546/276.7; 548/215, 243, 416, 427, 450; 514/339, 374, 514/378, 411
See application file for complete search history.

(56) References Cited

U.S. PATENT DOCUMENTS 6,018,068 A * 1/2000 Nagao et al. ............. 560/10
6,861,441 B1 * 3/2005 Clayton et al. .......... 514/411
6,924,297 B2 * 8/2005 Giblin et al. ............ 514/339

FOREIGN PATENT DOCUMENTS

EP    0 845 451      6/1988
WO    WO 00/18744    4/2000

* cited by examiner

*Primary Examiner*—Golam M. M. Shameem
(74) *Attorney, Agent, or Firm*—Grace C. Hsu; Mary E. McCarthy; Charles M. Kinzig

(57) ABSTRACT

Compounds of formula (I)

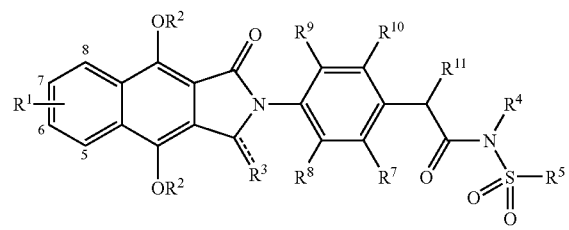

(I)

and pharmaceutically acceptable derivatives thereof bind with high affinity to the EP4 receptor and are of use in the treatment or prevention of conditions such as a pain, inflammatory, immunological, bone, neurodegenerative or renal disorder.

13 Claims, No Drawings

BENZO (F) INSOINDOL DERIVATIVES AND THEIR USE AS EP4 RECEPTOR LIGANDS

This invention relates to naphthalene derivatives, to processes for their preparation, to pharmaceutical compositions containing them and to their use in medicine.

The EP4 receptor is a 7-transmembrane receptor and its natural ligand is the prostaglandin $PGE_2$. $PGE_2$ also has affinity for the other EP receptors (types EP1, EP2 and EP3). The EP4 receptor is associated with smooth muscle relaxation, inflammation, lymphocyte differentiation, bone metabolism processes, allergic activities, promotion of sleep, renal regulation and gastric or enteric mucus secretion. We have now found a novel group of compounds which bind with high affinity to the EP4 receptor.

The invention thus provides compounds of the formula (I)

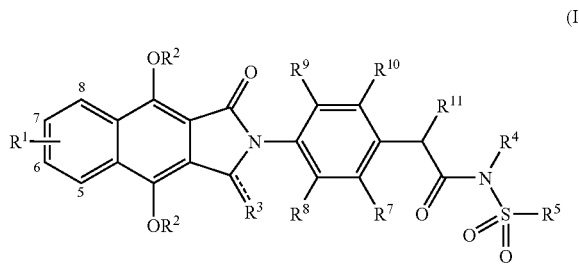

and pharmaceutically acceptable derivatives thereof in which:

$R^1$ is H, halogen, $C_{1-6}$alkyl, S—$C_{1-6}$alkyl, $C_{1-6}$alkoxy, $OCF_3$, $OCH_2CF_3$, O-cyclopropyl, $OCH_2$-cyclopropyl, $NH_2$, $NHC_{1-6}$alkyl, $N(C_{1-6}$alkyl$)_2$, $NO_2$, OH, $CH_2OC_{1-6}$alkyl or $CH_2OH$;

each $R^2$ is independently selected from $C_{1-4}$alkyl;

$R^3$ is H or O;

$R^4$ is H or $C_{1-6}$alkyl;

$R^5$ is $C_{1-6}$alkyl, phenyl, phenyl substituted by one or more $R^6$, naphthyl, phenyl$C_{1-6}$alkyl, pyridyl, oxazolyl, isoxazolyl, isoxazolyl substituted with one or two $C_{1-6}$alkyl, thiophenyl, $C_{1-6}$alkyl$CO_2C_{1-6}$alkyl, pyrrolyl, furanyl, thiazolyl, isothiazolyl, imidazolyl, pyrazolyl, thiadiazolyl, isothiadiazolyl, indolyl, indazolyl and benzothiophenyl;

$R^6$ is halogen, $C_{1-6}$alkyl, $C_{1-6}$alkyl substituted by one or more fluorine atoms, $C_{1-6}$alkoxy, cyano, $CO_2H$, $CO_2C_{1-6}$alkyl, OH, $NH_2$, $NHC_{1-6}$alkyl, $N(C_{1-6}$alkyl$)_2$, $S(O)_nC_{1-6}$alkyl where n=0, 1 or 2, $CONH_2$, $CON(C_{1-6}$alkyl$)_2$, $COC_{1-6}$alkyl or $NHCO(C_{1-6}$alkyl);

$R^7$ to $R^{10}$ are each independently selected from H, $C_{1-6}$alkyl, $C_{1-6}$alkoxy, $C_{1-6}$alkoxy substituted by one or more fluorine atoms, O-cyclopropyl, $OCH_2$-cyclopropyl, S—$C_{1-6}$alkyl, $NH_2$, $NHC_{1-6}$alkyl, $N(C_{1-6}$alkyl$)_2$, halogen, $NO_2$, OH, $CH_2OC_{1-6}$alkyl, $CH_2OH$;

$R^{11}$ is selected from H, OH, halogen, dihalogen, $NH_2$, $NHC_{1-6}$alkyl, $N(C_{1-6}$alkyl$)_2$, $C_{1-6}$alkyl, $C_{1-6}$dialkyl, $C_{1-6}$alkoxy, $NHCO(C_{1-6}$alkyl), or =O;

----- is a single bond or, when $R^3$ is O, a double bond.

By pharmaceutically acceptable derivative is meant any pharmaceutically acceptable salt or solvate of the compounds of formula (I), or any other compound which upon administration to the recipient is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds, and that the compounds of formula (I) may be derivatised at more than one position.

It will be appreciated that, for pharmaceutical use, the salts referred to above will be physiologically acceptable salts, but other salts may find use, for example in the preparation of compounds of formula (I) and the physiological acceptable salts thereof.

Pharmaceutically acceptable salts include those described by Berge, Bighley and Monkhouse, *J. Pharm. Sci.*, 1977, 66, 1–19. Suitable pharmaceutically acceptable salts include: acid addition salts formed with inorganic acids or organic acids, preferably inorganic acids e.g. hydrochlorides, hydrobromides, sulphates and acetates; and alkali metal salts, formed from the addition of alkali metal bases, such as alkali metal hydroxides e.g. sodium salts. Further representative examples of pharmaceutically acceptable salts include those formed from maleic, fumaric, benzoic, ascorbic, pamoic, succinic, bismethylenesalicylic, methanesulfonic, ethanedisulfonic, propionic, tartaric, salicylic, citric, gluconic, aspartic, stearic, palmitic, itaconic, glycolic, p-aminobenzoic, glutomic, benzenesulfonic, cyclohexylsulfamic, phosphoric and nitirc acids.

The term 'halogen' is used to represent fluorine, chlorine, bromine or iodine.

The term 'alkyl' as a group or part of a group means a straight or branched chain alkyl group, for example a methyl, ethyl, n-propyl, i-propyl, n-butyl, s-butyl or t-butyl group.

The terms 'alkoxy' as a group or as part of a group means a straight or branched chain alkyl group having an oxygen atom attached to the chain, for example a methoxy, ethoxy, n-propoxy, i-propoxy, n-butoxy, s-butoxy or t-butoxy group.

In one aspect of the invention $R^1$ is at the 6-position of the naphthalene ring, as defined in formula (I).

In another aspect of the invention $R^1$ is H or halogen.

In another aspect of the invention $R^1$ is H or bromine.

In another aspect of the invention each $R^2$ is ethyl.

In another aspect of the invention $R^3$ is H.

In another aspect of the invention $R^4$ is H or methyl.

In another aspect of the invention $R^5$ is $C_{1-3}$alkyl, phenyl, phenyl substituted by one to three $R^6$, 2-naphthyl, $C_{1-2}$alkylphenyl, 3-pyridyl, isoxazolyl substituted by two $C_{1-2}$alkyl, 2-thiophenyl or $C_{1-2}$alkyl$CO_2C_{1-2}$alkyl.

In another aspect of the invention $R^6$ is halogen, $C_{1-4}$alkyl, $C_{1-3}$alkyl substituted by one to three F, $C_{1-4}$alkoxy, cyano or $CO_2C_{1-3}$alkyl.

In another aspect of the invention each of $R^7$ to $R^{11}$ is hydrogen.

It is to be understood that the present invention covers all combinations of particular aspects of the invention as described hereinabove.

In a particular aspect of the invention there is provided a group of compounds of formula (I) (group A) wherein: $R^1$ is H or bromine; each $R^2$ is ethyl; $R^3$ is H; $R^4$ is H or methyl; $R^5$ is $C_{1-3}$alkyl, phenyl, phenyl substituted by one to three $R^6$, 2-naphthyl, $C_{1-2}$alkylphenyl, 3-pyridyl, isoxazolyl substituted by two $C_{1-2}$alkyl, 2-thiophenyl or $C_{1-2}$alkyl$CO_2C_{1-2}$alkyl; $R^6$ is halogen, $C_{1-4}$alkyl, $C_{1-3}$alkyl substituted by one to three F, $C_{1-4}$alkoxy, cyano or $CO_2C_{1-3}$alkyl; each of $R^7$ to $R^{11}$ is hydrogen.

Within group A, there is provided a further group of compounds (group A1) wherein: $R^1$ is H; each $R^2$ is ethyl; $R^3$ is H; $R^4$ is H; $R^5$ is phenyl, phenyl substituted by one to two $R^6$, 3-pyridyl, 2-thiophenyl or $C_{1-2}alkylCO_2C_{1-2}alkyl$; $R^6$ is halogen, methyl, methoxy or $CO_2methyl$; each of $R^7$ to $R^{11}$ is hydrogen.

Within groups A and A1 there are provided further groups of compounds wherein $R^1$ is at the 6-position of the naphthalene ring, as defined in formula (I).

It is to be understood that the present invention encompasses all isomers of formula (I) and their pharmaceutically acceptable derivatives, including all geometric, tautomeric and optical forms, and mixtures thereof (e.g. racemic mixtures).

In one aspect the invention provides the following compounds and pharmaceutically acceptable derivatives thereof:

N-{[4-(4,9-diethoxy-1-oxo-1,3-dihydro-2H-benzo[f]isoindol-2-yl)phenyl]acetyl}-4-fluorobenzenesulfonamide; and N-{2-[4-(4,9-diethoxy-1-oxo-1,3-dihydro-2H-benzo[f] isoindol-2-yl)phenyl]acetyl}benzenesulfonamide.

Since the compounds of the present invention, in particular compounds of formula (I), are intended for use in pharmaceutical compositions, it will be understood that they are each provided in substantially pure form, for example at least 50% pure, more suitably at least 75% pure and preferably at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Preferably, whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. In addition, different crystallisation conditions may lead to the formation of different polymorphic forms of crystalline products. This invention includes within its scope all polymorphic forms of the compounds of formula (I).

The compounds of the invention bind to the EP4 receptor and are therefore useful in treating EP4 receptor mediated diseases.

In view of their ability to bind to the EP4 receptor, the compounds of the invention are useful in the treatment of the disorders that follow. Thus, the compounds of formula (I) are useful as analgesics. For example they are useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention are particularly useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) are also useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome pigeon fancier's disease, farmer's lung, COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of formula (I) are also useful in the treatment of immunological diseases such as autoimmune diseases, immunological deficiency diseases or organ transplantation. The compounds of formula (I) are also effective in increasing the latency of HIV infection.

The compounds of formula (I) are also useful in the treatment of diseases of abnormal platelet function (e.g. occlusive vascular diseases).

The compounds of formula (I) are also useful for the preparation of a drug with diuretic action.

The compounds of formula (I) are also useful in the treatment of impotence or erectile dysfunction.

The compounds of formula (I) are also useful in the treatment of bone disease characterised by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, osteoalgia, osteopenia, cancer cacchexia, calculosis, lithiasis (especially urolithiasis), solid carcinoma, gout and ankylosing spondylitis, tendinitis and bursitis. In a further aspect compounds of formula (I) may be useful in inhibiting bone resorption and/or promoting bone generation.

The compounds of formula (I) are also useful for attenuating the hemodynamic side effects of NSAIDs and COX-2 inhibitors.

The compounds of formula (I) are also useful in the treatment of cardiovascular diseases such as hypertension or myocardiac ischemia; functional or organic venous insufficiency; varicose therapy; haemorrhoids; and shock states associated with a marked drop in arterial pressure (e.g. septic shock).

The compounds of formula (I) are also useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) are also useful in the treatment of neuroprotection and in the treatment of neurodegeneration following stroke, cardiac arrest, pulmonary bypass, traumatic brain injury, spinal cord injury or the like.

The compounds of formula (I) are also useful in the treatment of tinnitus.

The compounds of formula (I) are also useful in preventing or reducing dependence on, or preventing or reducing tolerance or reverse tolerance to, a dependence—inducing agent. Examples of dependence inducing agents include opioids (e.g. morphine), CNS depressants (e.g. ethanol), psychostimulants (e.g. cocaine) and nicotine.

The compounds of formula (I) are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of formula (I) are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

Certain of the compounds of the invention have been shown to be potent and selective EP4 receptor antagonists. Accordingly, in a further aspect of the invention, there is provided the use of compounds of formula (I) and pharmaceutically acceptable derivatives thereof in the treatment of disorders ameliorated by EP4 receptor antagonism.

It is to be understood that reference to treatment includes both treatment of established symptoms and prophylactic treatment, unless explicitly stated otherwise.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by the action of $PGE_2$ at EP4 receptors.

According to another aspect of the invention, we provide a compound of formula (I) or a pharmaceutically acceptable derivative thereof for use in the treatment of a condition which is ameliorated by EP4 receptor antagonism.

According to a further aspect of the invention, we provide a method of treating a human or animal subject suffering from a condition which is mediated by the action of $PGE_2$ at EP4 receptors which comprises administering to said subject an effective amount of a compound of formula (I) or a pharmaceutically acceptable derivative thereof.

According to a further aspect of the invention, we provide a method of treating a human or animal subject suffering from a condition which is ameliorated by an EP4 receptor antagonist which comprises administering to said subject an effective amount of a compound of formula (I) or a pharmaceutically acceptable derivative thereof.

According to a further aspect of the invention we provide a method of treating a human or animal subject suffering from a pain, inflammatory, immunological, bone, neurodegenerative or renal disorder, which method comprises administering to said subject an effective amount of a compound of formula (I) or a pharmaceutically acceptable derivative thereof.

According to another aspect of the invention, we provide the use of a compound of formula (I) or a pharmaceutically acceptable derivative thereof for the manufacture of a therapeutic agent for the treatment of a condition which is mediated by the action of $PGE_2$ at EP4 receptors.

According to another aspect of the invention, we provide the use of a compound of formula (I) or a pharmaceutically acceptable derivative thereof for the manufacture of a therapeutic agent for the treatment of a condition which is ameliorated by EP4 receptor antagonism.

According to another aspect of the invention we provide the use of a compound of formula (I) or a pharmaceutically acceptable derivative thereof for the manufacture of a therapeutic agent for the treatment or prevention of a condition such as a pain, inflammatory, immunological, bone, neurodegenerative or renal disorder.

The compounds of formula (I) and their pharmaceutically acceptable derivatives are conveniently administered in the form of pharmaceutical compositions. Such compositions may conveniently be presented for use in conventional manner in admixture with one or more physiologically acceptable carriers or excipients.

Thus, in another aspect of the invention, we provide a pharmaceutical composition comprising a compound of formula (I) or a pharmaceutically acceptable derivative thereof adapted for use in human or veterinary medicine.

The compounds of formula (I) and their pharmaceutically acceptable derivatives may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives.

For oral administration, the pharmaceutical composition may take the form of, for example, tablets (including sublingual tablets), capsules, powders, solutions, syrups or suspensions prepared by conventional means with acceptable excipients.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilising and/or dispersing agents. For administration by injection these may take the form of a unit dose presentation or as a multidose presentation preferably with an added preservative.

Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of th invention may be formulated with suitable polymeric or hydrophobic materials (for example as an emulsion in an acceptable oil) or ion exchange resins, or as sparingly soluble derivatives, for example, as a sparingly soluble salt.

The EP4 receptor compounds for use in the instant invention may be used in combination with other therapeutic agents, for example COX-2 inhibitors, such as celecoxib, rofecoxib, valdecoxib or parecoxib; 5-lipoxygenase inhibitors; NSAID's, such as diclofenac, indomethacin, nabumetone or ibuprofen; leukotriene receptor antagonists; DMARD's such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; EP1 receptor ligands; EP2 receptor ligands; EP3 receptor ligands; EP1 antagonists; EP2 antagonists and EP3 antagonists. When the compounds are used in combination with other therapeutic agents, the compounds may be administered either sequentially or simultaneously by any convenient route.

The invention thus provides, in a further aspect, a combination comprising a compound of, formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic ag nt active against the same disease state the dose of each compound may differ from that when the compound is used alone. Appropriate doses will be readily appreciated by those skilled in the art.

A proposed daily dosage of compounds of formula (I) or their pharmaceutically acceptable salts for the treatment of man is from 0.01 to 10 mg/kg body weight per day and more particularly 0.1 to 3 mg/kg body weight per day, calculated as the free base, which may be administered as a single or divided dose, for example one to four times per day The dose range for adult human beings is generally from 8 to 1000 mg/day, such as from 20 to 800 mg/day, preferably 35 to 200 mg/day, calculated as the free base.

The precise amount of the compounds of formula (I) administered to a host, particularly a human patient, will be the responsibility of the attendant physician. However, the dose employed will depend on a number of factors including the age and sex of the patient, the precise condition being treated and its severity, and the route of administration.

Compounds of formula (I) and pharmaceutically acceptable derivatives thereof may be prepared by any method known in the art for the preparation of compounds of analogous structure.

Compounds of formula (I) and pharmaceutically acceptable derivatives thereof may be prepared by a process which comprises:

(A), coupling a sulfonamide of formula (II)

or a protected derivative thereof with an acid of formula (III)

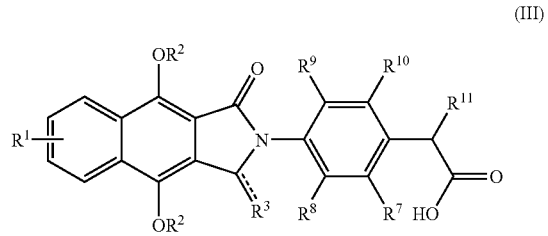

or a protected derivative thereof; or (B), interconversion of a compound of formula (I) into another compound of formula (I); or (C), deprotecting a protected derivative of compound of formula (I); and optionally converting compounds of formula (I) prepared by any one of the processes (A) to (C) into pharmaceutically acceptable derivatives thereof.

Suitable methods for the preparation of compounds of formula (I) and pharmaceutically acceptable derivatives thereof are described below, and form a further aspect of the invention. In the Schemes that follow $R^1$ to $R^{11}$ are as defined in formula (I) above unless otherwise stated; CDI is 1,1'-carbonyidiimidazole; DCM is dichloromethane; DIPEA is N,N-diisopropylethylamine; Hal is halogen, such as bromine or iodine; and Ac is acetyl.

Referring to Scheme 1 that follows, compounds of formula (I) may be prepared by coupling compounds of formula (III) with a sulfonamide of formula (II) in the presence of an activating agent, such as CDI, and a hindered organic amine base, such as DIPEA, In a suitable aprotic solvent such as DCM. Such couplings are described in many organic texts such as 'Principles of Peptide Synthesis' by Miklos Bodanszky (Springer Verlag, 1984) chapter 2, incorporated herein by reference.

Conveniently the hydrolysis of compounds of formula (IV) is effected using an inorganic base such as an alkali carbonate (e.g. potassium carbonate) in a suitable solvent such as an aqueous alcohol (e.g. aqueous ethanol), and at elevated temperature (e.g. from about 60° C. to reflux).

Scheme 1

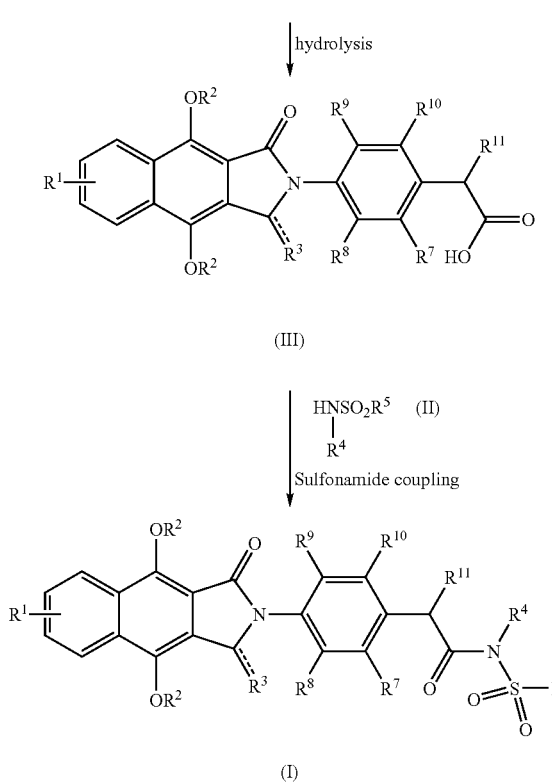

Compounds of formula (IV) wherein $R^3$ is H may be synthesised from the corresponding compounds of formula (IV) when $R^3$ is oxygen via reduction with a suitable reducing agent, for example zinc in acetic acid at elevated temperature.

Sulfonamides of formula (II) are either known compounds or may be prepared by literature methods such as those described in 'Advanced Organic Chemistry' by Jerry March, fourth edition (John Wiley & Sons, 1992) page 1296 column 2, incorporated herein by reference.

It will be appreciated by those persons skilled in the art that compounds of formula (I) may be prepared by interconversion, utilising other compounds of formula (I) as precursors. In particular, alkylations are well known to those skilled in the art and are described in many standard organic chemistry texts such as 'Advanced Organic Chemistry'. For example, compounds of formula (I) wherein $R^4$ is $C_{1-6}$alkyl can be prepared by alkylating compounds of formula (I) wherein $R^4$ is H.

As will be appreciated by those skilled in the art it may be necessary or desirable at any stage in the synthesis of compounds of formula (I) to protect one or more sensitive groups in the molecule so as to prevent undesirable side reactions. The protecting groups used in the preparation of compounds of formula (I) may be used in conventional manner. See, for example, those described in 'Protective Groups in Organic Synthesis' by Theodora W Green and Peter G M Wuts, second edition (John Wiley and Sons, 1991), incorporated herein by reference, which also describes methods for the removal of such groups.

Compounds of formula (IV), when $R^3$ is oxygen, may, for example, be prepared according to Scheme 2 that follows.

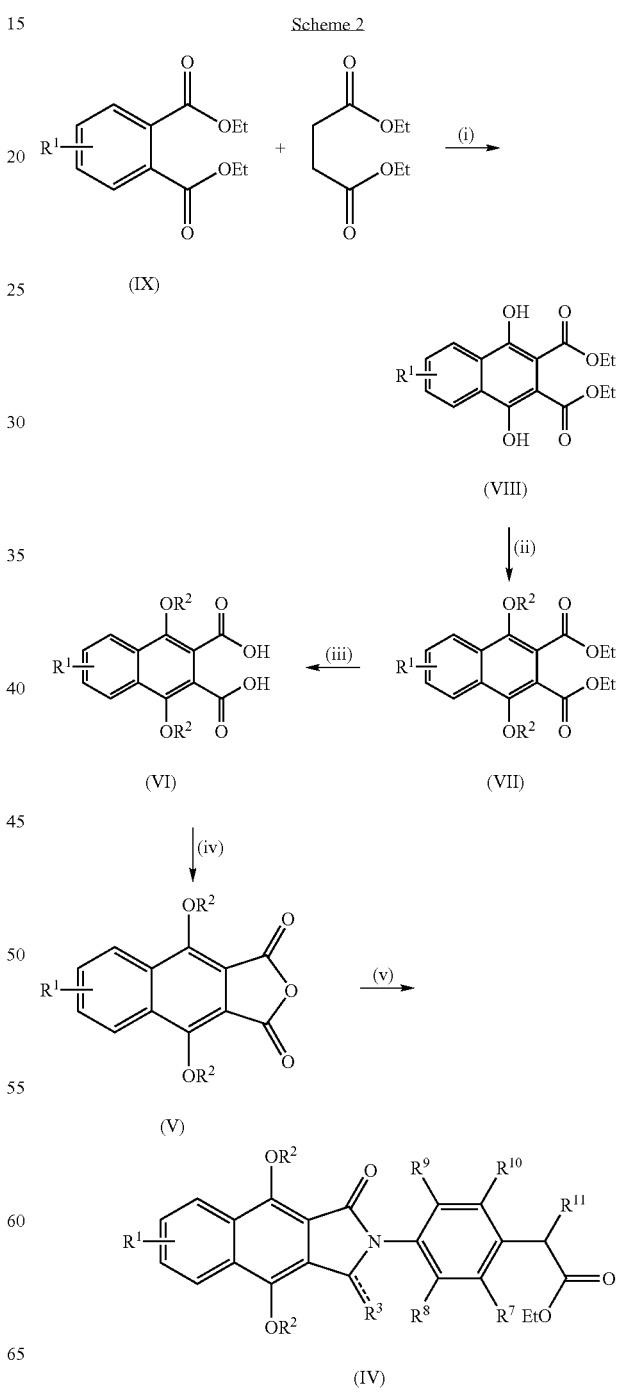

(i) Na, EtOH; (ii) K$_2$CO$_3$, R$^2$Hal, acetone; (iii) NaOH, aq. EtOH;
(iv) SOCl$_2$, CHCl$_3$; (v) 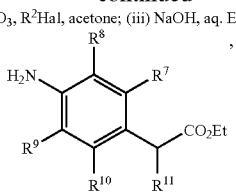, AcOH Phthalates of formula (IX) are either known compounds or may be prepared by conventional chemistry from commercially available starting materials.

Certain intermediates described above are novel compounds, and it is to be understood that all novel intermediates herein form further aspects of the present invention.

Solvates (e.g. hydrates) or salts of a compound of the invention may be formed during the work-up procedure of any one of the aforementioned process steps.

The Intermediates and Examples that follow illustrate the invention but do not limit the invention in any way. All temperatures are in ° C. $^1$H nmr spectra were obtained at 400 MHz on a Bruker DPX400. Mass directed autopurification was performed using a system comprising a HP1100 HPLC, a Gilson Aspec Autosampler, a HP1050 Make up Pump, a Micromass Platform Mass Spectrometer, a LC Packings Prep Accurate Combi-Chem Flow Processor (ACM-01-10), a Supelco 5 um ABZ+5 cm×10 mm ID Column and a Gilson Fraction Collector. The samples were dissolved in 50:50 acetonitrile:dimethylsulfoxide. A suitable gradient elution determined on the basis of the retention time of the compound in LC/MS was employed, for example 20–50% acetonitrile or 30–60% acetonitrile in water. The determination of such gradient elutions will be appreciated by those skilled in the art.

Intermediate 1

Ethyl 1,4-dihydroxy-2,3-naphthalenedicarboxylate

Sodium (60 g, 2.6 mol) was dissolved in ethanol (1.2 L) and the mixture was cooled to 40° C. Diethylphthalate (960 ml, 4.83 mol) was added and the mixture heated under nitrogen until the temperature reached 115° C. Diethyl succinate (211.3 g, 1.21 mol) was added dropwise over 45 min. The reaction was heated at 115° C. for a further 45 min, cooled to room temperature and poured onto water (1.2 L). Ethyl acetate (1 L) was added and stirred, the layers were separated and the organics were extracted with sodium hydroxide solution (2N, 1 L). The combined aqueous was acidified to pH 3 and the mixture extracted with ethyl acetate (2×1 L). The combined organics were washed with a saturated solution of sodium hydrogen carbonate (2×1.5 L), then brine, dried (MgSO$_4$), filtered and the solvent evaporated under vacuum. The residue was purified using a 2.5 kg Biotage column eluting with 5% ethyl acetate/hexane to give the title compound as a white solid, (60 g, 16%)

δH CDCl$_3$ 10.44,(2H, s), 8.34,(2H, m), 7.68,(2H, m), 4.37,(4H, q), 1.37,(6H, t).

Intermediate 2

Ethyl 1,4-diethoxy-2,3-naphthalenedicarboxylate

Ethyl 1,4-dihydroxy-2,3-naphthalenedicarboxylate (30 g, 98.6 mmol) and potassium carbonate (150 g, 1.09 mmol) were stirred in acetone (600 ml) under nitrogen. Iodoethane (150 g, 0.96 mol) was added and the mixture was stirred at reflux overnight. The reaction was cooled, diluted with ethyl acetate and filtered. The filtrate was evaporated to leave a brown oil, which was dissolved in toluene and washed with potassium hydroxide solution (5%, 150 ml) and brine. Drying over magnesium sulphate and evaporation of the solvent gave a yellow solid. Purification using an 800 g Biotage column gave the title compound as a white solid (32 g, 90%).

δH CDCl$_3$ 8.16,(2H, m), 7.60,(2H, m), 4.40,(4H, q), 4.18,(4H, q), 1.50,(6H, t), 1.40,(6H, t).

Intermediate 3

1,4-Diethoxy-2,3-naphthalenedicarboxylic acid

Ethyl 1,4-diethoxy-2,3-naphthalenedicarboxylate (32 g, 89 mmol) was added to a solution of sodium hydroxide (20 g) in ethanol (200 ml) and water (40 ml) and stirred for 1.5 h at 60° C. The reaction was cooled and the thick white suspension was filtered. The solid was dissolved in a mixture of ethyl acetate (200 ml) and water (800 ml). The layers were separated and the aqueous was acidified with hydrochloric acid (2M, 120 ml). The aqueous was extracted with ethyl acetate (2×) and the combined organics were dried (MgSO$_4$). Evaporation of the solvent under vacuum gave the title compound as a white solid (25 g, 92%).

δH [$^2$H$_6$]—DMSO 13.26,(2H, s), 8.15,(2H, m), 7.72,(2H, m), 4.13,(4H, q), 1.42,(6H, t).

Intermediate 4

1,4-Diethoxy-2,3-naphthalenedicarboxylic anhydride 1,4-Diethoxy-2,3-naphthalenedicarboxylic acid (25 g, 82 mmol) was added to a solution of thionyl chloride (23.3 g) in chloroform (150 ml) and stirred at reflux for 1 h. The resulting solution was cooled and evaporated to dryness. Further chloroform was added and evaporation repeated to give the title compound as a yellow solid (23.3 g, 99%).

δH [$^2$H$_6$]—DMSO 8.42,(2H, m), 7.93,(2H, m), 4.53,(4H, q), 1.46,(6H, t).

Intermediate 5

Ethyl[4-(4,9-diethoxy-1,3-dioxo-1,3-dihydro-2H-benzo[f]isoindol-2-yl)phenyl]acetate 1,4-Diethoxy-2,3-naphthalenedicarboxylic anhydride (23.3 g, 81.5 mmol) and ethyl (4-aminophenyl)acetate (14.8 g, 82 mmol) were refluxed under nitrogen in acetic acid (160 ml) overnight. The mixture was cooled to room temperature and poured into water (1 L). The white solid was filtered, washed with water and dissolved in dichloromethane (800 ml). The solution was washed with water, brine and dried (MgSO$_4$) and the solvent evaporated under vacuum to give the title compound as an off-white solid (33 g, 96%).

δH [$^2$H$_6$]—DMSO 8.40,(2H, m), 7.87,(2H, m), 7.42,(4H, s), 4.47,(4H, q), 4.12,(2H, q), 3.76,(2H, s), 1.45,(6H, t), 1.21,(3H, t).

Intermediate 6

Ethyl [4-(4,9-diethoxy-1-oxo-1,3-dihydro-2H-benzo[f]isoindol-2-yl)phenyl]acetate Ethyl [4-(4,9-diethoxy-1,3-dioxo-1,3-dihydro-2H-benzo[f]isoindol-2-yl)phenyl]acetate (33 g, 73 mmol) and zinc (90 g, 1.38 mol) were refluxed in acetic acid for 66 h. An additional quantity of zinc (25 g, 0.38 mol) was added and reflux continued for 18 h. The mixture was filtered hot and the filtrate was evaporated to a yellow solid. The solid was purified by 800 g Biotage column eluting with 20% ethyl acetate/hexane to give a white solid, which was triturated in ether to give a white solid. A further fraction was obtained by crystallisation from the ether residues. A total of 10.2 g, 32% of the title compound was obtained.

δH CDCl$_3$ 8.42,(1H, d), 8.18,(1H, d), 7.88,(2H, d), 7.63, (2H, m), 7.38,(2H, d), 5.00,(2H, s), 4.51,(2H, q), 4.26,(2H, q), 4.18,(2H, q), 3.65,(2H, s), 1.57, (6H, m), 1.28,(3H, t).

Intermediate 7

[4-(4,9-diethoxy-1-oxo-1,3-dihydro-2H-benzo[f]isoindol-2-yl)phenyl]acetic acid Ethyl [4-(4,9diethoxy-1-oxo-1,3-dihydro-2H-benzo[f]isoindol-2-yl)phenyl]acetate (5.86 g, 13.5 mmol) and potassium carbonate (12 g) were added td a mixture of ethanol (146 ml) and water (70 ml) and heated to reflux for 2 h. The solution was cooled to room temperature and the solvent evaporated under vacuum to leave an off-white solid. The solid was slurried in water and the water was evaporated under vacuum. The residue was stirred in hydrochloric acid (2N) for 2 h, filtered and washed with water. Drying of the solid at 40° C. in a vacuum oven gave the title compound as a white solid (4.5 g, 82%)

δH [$^2$H$_6$]—DMSO 12.27,(1H, b), 8.25,(1H, d), 8.12,(1H, d), 7.86,(2H, d), 7.61,(2H, m), 7.27,(2H, d), 5.10,(2H, s), 4.34,(2H, q), 4.25,(2H, q), 3.54, (2H, s), 1.41,(3H, t), 1.37,(3H, t). MS 406, [MH$^+$]

EXAMPLE 1

N-{[4-(4,9-diethoxy-1-oxo-1,3-dihydro-2H-benzo[f]isoindol-2-yl)phenyl]acetyl}-4-fluorobenzenesulfonamide To a solution of carbonyldiimidazole (13.2 mg, 0.081 mmol) and [4-(4,9-diethoxy-1-oxo-1,3-dihydro-2H-benzo[f]isoindol-2-yl)phenyl]acetic acid (30 mg, 0.074 mmol) in dichloromethane (2 ml) was added 4-fluorobenzenesulphonamide (14.3 mg, 0.081 mmol) and N,N-diisopropylethylamine (10.5 mg, 0.81 mmol). The mixture was stirred at ambient temperature under an atmosphere of nitrogen overnight. The reaction mixture was diluted with dichloromethane (3 ml) and then washed with 2N hydrochloric acid (5 ml). The organic phase was dried (MgSO$_4$) and then concentrated in vacuo to give a brown gum. The residue was purified using mass directed autopurification to give the title compound as a white solid (14.7 mg, 35.3%). MH+563.

The examples of Table 1 were prepared in the manner described for Example 1.

TABLE 1

(I)

| Ex | R$^1$ | R$^2$ | R$^3$ | R$^4$ | R$^5$ | R$^7$ to R$^{11}$ | MS |
|---|---|---|---|---|---|---|---|
| 2 | H | ethyl | H | H | 3,4-dichlorophenyl | H | MH$^+$ 614 |
| 3 | H | ethyl | H | H | phenyl | H | MH$^+$ 545 |
| 4 | H | ethyl | H | H | 2-methylphenyl | H | MH$^+$ 559 |
| 5 | H | ethyl | H | H | 3-trifluoromethylphenyl | H | MH$^+$ 613 |
| 6 | H | ethyl | H | H | 4-ethylphenyl | H | MH$^+$ 573 |
| 7 | H | ethyl | H | H | 4-cyanophenyl | H | NH$^+$ 570 |
| 8 | H | ethyl | H | H | 3-chlorophenyl | H | MH$^+$ 579 |
| 9 | H | ethyl | H | H | 2-methoxy-4-methylphenyl | H | MH$^+$ 589 |
| 10 | H | ethyl | H | H | 3-bromophenyl | H | MH$^+$ 623 |
| 11 | H | ethyl | H | H | 2,5-dimethoxyphenyl | H | MH$^+$ 605 |
| 12 | H | ethyl | H | H | 5-bromo-2-methoxyphenyl | H | MH$^+$ 654/656 |
| 13 | H | ethyl | H | H | 3-methoxyphenyl | H | MH$^+$ 575 |
| 14 | H | ethyl | O | H | 2-methylphenyl | H | MH$^+$ 573 |
| 15 | H | ethyl | O | H | phenyl | H | MH$^+$ 559 |
| 16 | H | ethyl | O | H | 3-chlorophenyl | H | MH$^+$ 593 |
| 17 | H | ethyl | O | H | 3-methoxyphenyl | H | MH$^+$ 589 |
| 18 | H | ethyl | O | H | 5-bromo-2-methoxyphenyl | H | MH$^+$ 667/669 |
| 19 | H | ethyl | O | H | 2-methylcarboxyphenyl | H | MH$^-$ 615 |
| 20 | H | ethyl | O | H | 2,5-dimethoxyphenyl | H | MH$^+$ 619 |
| 21 | H | ethyl | O | H | 2-fluorophenyl | H | MH$^+$ 577 |
| 22 | H | ethyl | O | H | 2,5-difluorophenyl | H | MH$^+$ 595 |
| 23 | H | ethyl | O | H | 4-tert-butylphenyl | H | MH$^+$ 615 |
| 24 | H | ethyl | O | H | 3-bromophenyl | H | MH$^+$ 637/639 |
| 25 | H | ethyl | O | H | 4-butoxyphenyl | H | MH$^+$ 631 |
| 26 | H | ethyl | O | H | 2-methoxy-4-methylphenyl | H | MH$^+$ 603 |
| 27 | H | ethyl | O | CH$_3$ | 2,5-dimethoxyphenyl | H | MH$^+$ 633 |
| 28 | Br | ethyl | O | H | 4-fluorophenyl | H | MH$^+$ 655/657 |
| 29 | H | ethyl | H | H | benzyl | H | MH$^+$ 559 |
| 30 | H | ethyl | H | H | 3-pyridyl | H | MH$^+$ 546 |
| 31 | H | ethyl | H | H | 3,5-dimthylisoxazol-4-yl | H | MH$^+$ 564 |
| 32 | H | ethyl | H | H | methyl | H | MH$^+$ 483 |
| 33 | H | ethyl | H | H | phenethyl | H | MH$^+$ 573 |
| 34 | H | ethyl | H | H | CH$_2$CO$_2$C$_2$H$_5$ | H | MH$^+$ 555 |
| 35 | H | ethyl | H | H | 2-thiophenyl | H | MH$^+$ 551 |
| 36 | H | ethyl | O | H | 2-thiophenyl | H | MH$^+$ 565 |
| 37 | H | ethyl | H | H | 2-naphthyl | H | MH$^+$ 595 |

Biological Data

The ability of the compounds to bind to EP4 receptors may be demonstrated in the Human EP$_4$ Scintillation Proximity Assay.

Quantification of radioligand binding by scintillation proximity assay (SPA) is a long-established principle.

Briefly, the affinity of compounds for a receptor is assesssed by the specific competition between known quantities of radiolabelled ligand and compound for that receptor. Increasing concentrations of compound reduce the amount of radiolabel that binds to the receptor. This gives rise to a diminishing scintillation signal from SPA beads coated with membranes that bear the receptor. The signal may be detected with a suitable scintillation counter and the data generated may be analysed with suitable curve-fitting software.

The human $EP_4$ SPA assay (hereafter referred to as 'the assay') utilises membranes prepared from Chinese Hamster Ovary (CHO cells) infected with Semilki Forest Virus (SFV). Genetically engineered SFV-1 viral particles containing the genetic sequence of the human EP4 receptor were used to infect CHO cells resulting in expression of the receptor protein in cellular membranes. Cells washed free of media are homogenised in a pH-buffered medium containing peptidase inhibitors. A suitable buffer is of the following composition: 50 mM HEPES, 1 mM EDTA, 25 µg/ml bacitracin, 100 µM leupeptin, 1 mM PMSF, 2 µM Pepstatin A, pH adjusted to 7.4 with KOH. Following removal of cell debris by a low-speed centrifugation, a pellet of membranes is prepared by a high-speed (48000 g) centrifugation of the resulting supernatant. Membrane suspensions such as that described may be stored at −80° C. until used.

For assay, membranes expressing human $EP_4$ receptors are diluted in a pH-buffered medium and mixed with SPA beads coated with a suitable substance to facilitate the adhesion of membranes to the beads. The concentrations of membrane protein and SPA beads chosen should result in SPA binding signal of at least 300 corrected counts per minute (CCPM) when tritiated radioligand at a concentration close to its $K_d$ (affinity value) is combined with the mixture. Non-specific binding (nsb) may be determined by competition between the radiolabelled ligand and a saturating concentration of unlabelled ligand. In order to quantify the affinity of EP4 receptor ligands, compounds are diluted in a stepwise manner across the wells of a 96-well plate. Radioligand, compound, and unlabelled ligand are then added to a 96-well plate suitable for the measurement of SPA binding signals prior to the addition of bead/membrane mixture to initiate the binding reaction. Equilibrium may be achieved by incubation at room temperature for 120 minutes prior to scintillation counting. The data so generated may be analysed by means of a computerised curve-fitting routine in order to quantify the concentration of compound that displaces 50% of the specific radioligand binding ($IC_{50}$). The affinity ($pK_i$) of the compound may be calculated from the $IC_{50}$ by application of the Cheng-Prusoff correction. Suitable reagents and protocols are: reaction buffer containing 50 mM HEPES, 10 mM $MgCl_2$, pH adjusted to 7.4 with KOH; SPA beads coated with wheatgerm agglutinin; 1.25 nM [$^3$H]-prostaglandin $E_2$ as radioligand; 10 µM prostaglandin $E_2$ as unlabelled ligand; a three-fold dilution series of compound starting at 10 µM and ending at 0.3 nM is adequate.

The ability of the compounds to antagonise EP4 receptors may be demonstrated in the [$^{125}$I]cAMP Scintillation Proximity Assay (hereafter referred to as 'the cAMP assay'). The CAMP assay utilises HEK-293 cells expressing the recombinant human EP4 receptor, obtained from Receptor Biology, Inc. Beltsville, Md., USA. The cells were cultured in Dulbecco's Modified Eagle Medium—HAM F12 mix (DMEM-F12), containing 10% heat inactivated-foetal bovine serum (FBS) and 2 mM L-glutamine. The cells were either passaged into fresh medium or used in an assay once 90% confluency as determined visually had been achieved.

The cells were harvested by treatment with Versene, re-suspended in fresh culture medium and plated out to yield approximately 10,000 cells per well of a 96-well plate for overnight culture in culture medium additionally supplemented with 3 µM indomethacin. For assay, the culture medium was replaced with assay medium (DMEM-F12 containing 300 µM isobutylmethylxanthine (IBMX) and 3 µM indomethacin) and incubated for 30 minutes. Following this, antagonist was then added at various concentrations such that an entire agonist concentration-effect curve could be obtained in the presence of a single concentration of the antagonist. The antagonist was allowed to equilibrate with the cells for 30 minutes. Subsequently the cells were challenged with an agonist for 15 minutes. The reaction was stopped by the aspiration of the assay medium and the addition of ice-cold ethanol. All incubations were carried out at 37 C in a 5% carbon dioxide atmosphere. Care was taken to ensure the constancy of IBMX, indomethacin and vehicle (DMSO) concentrations throughout. The amount of cAMP in each well was then determined by [$^{125}$I]cAMP scintillation proximity assay using a proprietary kit, obtained from Amersham, Buckinghamshire, UK, and according to the manufacturers instructions.

Data from cAMP assays were expressed as pmol CAMP per well. A four-parameter logistic equation of the form:

$$E=((Em.[A])^{nH})/((EC_{50}{}^{nH})+([A]^{nH}))$$

was then fitted to E/[A] curve data in order to estimate maximum effect (Em), curve mid-point (EC50), and Hill slope (nH); other terms in the equation are effect (E) and concentration ([A]). Individual estimates of curve parameters were obtained from each curve. An empirical estimate of antagonist affinity ($pA_2$) could then be obtained using the following formula:

$$pA_2=\log((EC_{50}{}^B/EC_{50}{}^A)-1)-\log[B]$$

where $EC_{50}{}^A$ is the midpoint of a control agonist concentration-effect curve in the absence of antagonist; $EC_{50}{}^B$ is the midpoint of an agonist concentration effect curve produced in the presence of a fixed concentration of antagonist; and [B] is the concentration of antagonist used. Estimates from individual experiments were then averaged to provide mean data. Quoted values are therefore the mean±standard deviation (s.d.) of n separate experiments, each derived from a separate cAMP assay.

For the rigorous estimation of antagonist affinity values ($pK_b$) the method of Arunlakshana and Schild was employed. Briefly, the midpoint of agonist concentration/effect curves in the presence and absence of antagonist are used to calculate concentration ratios (CR). Linear regression is performed on a plot of (CR-1) against concentration of antagonist (−log [B]) in order to estimate the point of intersection with the concentration (−log[B]) axis and the slope of the line. If the slope of the regression does not differ significantly from unity then it may be constrained to 1.0. Under this latter circumstance, the point of intersection on the concentration axis represents the affinity ($pK_b$) of the antagonist.

The following examples have a $pK_i$ of 7.0 or greater at EP4 receptors as determined using the above-mentioned procedure:
1, 3, 4, 9, 10, 12, 13, 14, 15, 16, 30, 34, 35 and 37.

Examples 1 and 3 were tested in the above-mentioned EP4 antagonist assay and both were shown to have a $pK_b$ of 7.0 or greater.

What is claimed is:

1. A compound of formula (I):

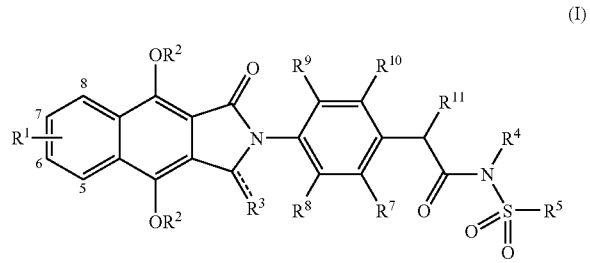

(I)

and pharmaceutically acceptable derivatives thereof wherein:
- $R^1$ is selected from the group consisting of H, halogen, $C_{1-6}$alkyl, $S-C_{1-6}$alkyl, $C_{1-6}$alkoxy, $OCF_3$, $OCH_2CF_3$, O-cyclopropyl, $OCH_2$-cyclopropyl, $NH_2$, $NHC_{1-6}$alkyl, $N(C_{1-6}alkyl)_2$, $NO_2$, OH, $CH_2OC_{1-6}$alkyl and $CH_2OH$;
- $R^2$ each independently selected from $C_{1-4}$alkyl;
- $R^3$ is H or O;
- $R^4$ is H or $C_{1-6}$alkyl;
- $R^5$ is selected from the group consisting of $C_{1-6}$alkyl, phenyl, phenyl substituted by one or more $R^6$, naphthyl, phenyl$C_{1-6}$alkyl, pyridyl, oxazolyl, isoxazolyl, isoxazolyl substituted with one or two $C_{1-6}$alkyl, thiophenyl, $C_{1-6}$alkyl$CO_2C_{1-6}$alkyl, pyrrolyl, furanyl, thiazolyl, isothiazolyl, imidazolyl, pyrazolyl, thiadiazolyl, isothiadiazolyl, indolyl, indazolyl, and benzothiophenyl;
- $R^6$ is selected from the group consisting of halogen, $C_{1-6}$alkyl, $C_{1-6}$alkyl substituted by one or more fluorine atoms, $C_{1-6}$alkoxy, cyano, $CO_2H$, $CO_2C_{1-6}$alkyl, OH, $NH_2$, $NHC_{1-6}$alkyl, $N(C_{1-6}alkyl)_2$, $S(O)_nC_{1-6}$alkyl wherein n=0, 1 or 2, $CONH_2$, $CON(C_{1-6}alkyl)_2$, $COC_{1-6}$ alkyl, and $NHCO(C_{1-6}alkyl)$;
- $R^7$ to $R^{10}$ each independently are selected from the group consisting of H, $C_{1-6}$alkyl, $C_{1-6}$alkoxy, $C_{1-6}$alkoxy substituted by one or more fluorine atoms, O-cyclopropyl, $OCH_2$-cyclopropyl, $S-C_{1-6}$alkyl, $NH_2$, $NHC_{1-6}$alkyl, $N(C_{1-6}alkyl)_2$, halogen, $NO_2$, OH, $CH_2OC_{1-6}$alkyl, and $CH_2OH$;
- $R^{11}$ is selected from the group consisting of H, OH, halogen, dihalogen, $NH_2$, $NHC_{1-6}$alkyl, $N(C_{1-6}alkyl)_2$, $C_{1-6}$alkyl, $C_{1-6}$dialkyl, $C_{1-6}$alkoxy, $NHCO(C_{1-6}alkyl)$, and =O; and provided that
----- is a single bond, when $R^3$ is O, a double bond.

2. The compound according to claim 1, wherein each $R^2$ is H or bromine.

3. The compound according to claim 1, wherein each $R^2$ is ethyl.

4. The compound according to claim 1, wherein $R^3$ is H.

5. The compound according to claim 1, wherein $R^4$ is H or methyl.

6. The compound according to claim 1, wherein $R^5$ is selected from the group consisting of $C_{1-3}$alkyl, phenyl, phenyl substituted by one to three $R^6$, 2-naphthyl, phenyl$C_{1-2}$alkyl, 3-pyridyl, isoxazolyl substituted by two $C_{1-2}$alkyl, 2-thiophenyl, and $C_{1-2}$alkyl$CO_2C_{1-2}$alkyl.

7. The compound according to claims 1, wherein $R^6$ is selected from the group consisting of halogen, $C_{1-4}$alkyl, $C_{1-3}$alkyl substituted by one to three F, $C_{1-4}$alkoxy, cyano, and $CO_2C_{1-3}$alkyl.

8. The compound according to claim 1, wherein $R^1$ is at the 6-position of the naphthalene ring, as claimed in formula (I).

9. The compound according to claim 1, wherein:
- $R^1$ is H;
- each $R^2$ is ethyl;
- $R^3$ is H;
- $R^4$ is H;
- $R^5$ is selected from the group consisting of phenyl, phenyl substituted by one to two $R^6$, 3-pyridyl, 2-thiophenyl, and $C_{1-2}$alkyl$CO_2C_{1-2}$alkyl;
- $R^6$ is selected from the group consisting of halogen, methyl, methoxy, and $CO_2$methyl; and
- each of $R^7$ to $R^{11}$ is hydrogen.

10. A compound of formula (I) according to claim 1:

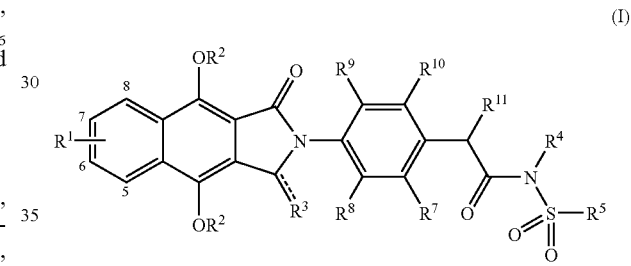

(I)

wherein said compound is selected from the group consisting of:

| Example | $R^1$ | $R^2$ | $R^3$ | $R^4$ | $R^5$ | $R^7$ to $R^{11}$ |
|---|---|---|---|---|---|---|
| 1 | H | ethyl | H | H | 4-fluorophenyl | H |
| 2 | H | ethyl | H | H | 3,4-dichlorophenyl | H |
| 3 | H | ethyl | H | H | phenyl | H |
| 4 | H | ethyl | H | H | 2-methylphenyl | H |
| 5 | H | ethyl | H | H | 3-trifluoromethylphenyl | H |
| 6 | H | ethyl | H | H | 4-ethylphenyl | H |
| 7 | H | ethyl | H | H | 4-cyanophenyl | H |
| 8 | H | ethyl | H | H | 3-chlorophenyl | H |
| 9 | H | ethyl | H | H | 2-methoxy-4-methylphenyl | H |
| 10 | H | ethyl | H | H | 3-bromophenyl | H |
| 11 | H | ethyl | H | H | 2,5-dimethoxyphenyl | H |
| 12 | H | ethyl | H | H | 5-bromo-2-methoxyphenyl | H |
| 13 | H | ethyl | H | H | 3-methoxyphenyl | H |
| 14 | H | ethyl | O | H | 2-methylphenyl | H |
| 15 | H | ethyl | O | H | phenyl | H |
| 16 | H | ethyl | O | H | 3-chlorophenyl | H |
| 17 | H | ethyl | O | H | 3-methoxyphenyl | H |
| 18 | H | ethyl | O | H | 5-bromo-2-methoxyphenyl | H |
| 19 | H | ethyl | O | H | 2-methylcarboxyphenyl | H |
| 20 | H | ethyl | O | H | 2,5-dimethoxyphenyl | H |
| 21 | H | ethyl | O | H | 2-fluorophenyl | H |
| 22 | H | ethyl | O | H | 2,5-difluorophenyl | H |

-continued

| Example | R¹ | R² | R³ | R⁴ | R⁵ | R⁷ to R¹¹ |
|---|---|---|---|---|---|---|
| 23 | H | ethyl | O | H | 4-tert-butylphenyl | H |
| 24 | H | ethyl | O | H | 3-bromophenyl | H |
| 25 | H | ethyl | O | H | 4-butoxyphenyl | H |
| 26 | H | ethyl | O | H | 2-methoxy-4-methyl-phenyl | H; |
| 27 | H | ethyl | O | CH₃ | 2,5-dimethoxyphenyl | H |
| 28 | Br | ethyl | O | H | 4-fluorophenyl | H |
| 29 | H | ethyl | H | H | benzyl | H |
| 30 | H | ethyl | H | H | 3-pyridyl | H |
| 31 | H | ethyl | H | H | 3,5-dimethylisoxazol-4-yl | H |
| 32 | H | ethyl | H | H | methyl | H |
| 33 | H | ethyl | H | H | phenethyl | H |
| 34 | H | ethyl | H | H | CH₂CO₂C₂H₅ | H |
| 35 | H | ethyl | H | H | 2-thiophenyl | H |
| 36 | H | ethyl | O | H | 2-thiophenyl | H; and |
| 37 | H | ethyl | H | H | 2-naphthyl | H |

11. A process for preparation of compounds of formula (I) and pharmaceutically acceptable derivatives thereof as claimed in claim 1, wherein said process comprises:

(A), coupling a sulfonamide of formula (II)

or a protected derivative thereof with an acid of formula (III)

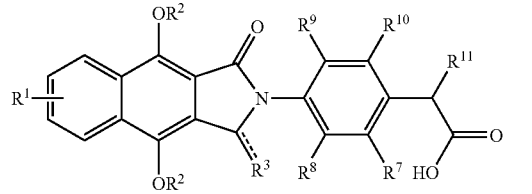

or a protected derivative thereof; or (B), interconverting a compound of formula (I) into another compound of formula (I); or (C), deprotecting a protected derivative of compound of formula (I); and optionally converting compounds of formula (I) prepared by any one of processes or process steps (A) to (C) into pharmaceutically acceptable derivatives thereof.

12. A pharmaceutical composition, comprising a compound of formula (I) or a pharmaceutically acceptable derivative thereof as claimed in claim 1 in admixture with one or more physiologically acceptable carriers or excipients.

13. A compound of formula (I) or a pharmaceutically acceptable derivative thereof as claimed in claim 1 for use in human or veterinary medicine.

* * * * *